(12) United States Patent
McMahon

(10) Patent No.: US 7,825,266 B1
(45) Date of Patent: Nov. 2, 2010

(54) EXTRACTION OF FULVIC MINERALS FROM HUMIC SUBSTANCES

(76) Inventor: Geoff McMahon, P.O. Box 9, Farmington, NM (US) 87499

( * ) Notice: Subject to any disclaimer, the term of this patent is extended or adjusted under 35 U.S.C. 154(b) by 1208 days.

(21) Appl. No.: 11/155,449

(22) Filed: Jun. 15, 2005

Related U.S. Application Data

(60) Provisional application No. 60/580,070, filed on Jun. 15, 2004.

(51) Int. Cl.
*C07D 319/00* (2006.01)
*C05F 11/02* (2006.01)

(52) U.S. Cl. .................. 549/359; 71/24; 71/64.1; 426/531

(58) Field of Classification Search ............... 71/11–27, 71/64.1; 549/359
See application file for complete search history.

(56) References Cited

U.S. PATENT DOCUMENTS

| | | | |
|---|---|---|---|
| 2,027,766 A | | 1/1936 | Davis et al. |
| 2,992,093 A | * | 7/1961 | Burdick .................. 71/24 |
| 3,111,404 A | | 11/1963 | Karcher et al. |
| 3,321,296 A | * | 5/1967 | Abbe ..................... 71/24 |
| 3,398,186 A | * | 8/1968 | Schwartz ................ 562/405 |
| 3,418,100 A | | 12/1968 | Cooley et al. |
| 3,544,296 A | | 12/1970 | Karcher |
| 3,630,710 A | | 12/1971 | Frederickson |
| 3,872,002 A | | 3/1975 | Musgrove |
| 3,985,536 A | * | 10/1976 | Abbe et al. .............. 71/24 |
| 4,069,034 A | * | 1/1978 | Hoover .................. 71/33 |
| 4,459,149 A | * | 7/1984 | Moran et al. ............ 71/24 |
| 4,778,602 A | | 10/1988 | Allen, III |
| 4,786,307 A | | 11/1988 | Marihart |
| 4,861,481 A | | 8/1989 | Allen, III |
| 5,178,661 A | | 1/1993 | van der Watt et al. |
| 5,451,240 A | * | 9/1995 | Trowbridge ............. 71/24 |
| 5,466,273 A | | 11/1995 | Connell |
| 6,080,220 A | * | 6/2000 | Sequi et al. ............. 71/11 |
| 6,147,229 A | * | 11/2000 | Rasmussen et al. ...... 549/393 |
| 6,204,396 B1 | * | 3/2001 | Rasmussen et al. ...... 549/393 |
| 6,461,399 B1 | | 10/2002 | Connell |
| 6,471,741 B1 | | 10/2002 | Reinbergen |
| 6,478,946 B1 | | 11/2002 | Westwood |
| 6,695,892 B1 | | 2/2004 | Fischer et al. |
| 6,696,577 B1 | * | 2/2004 | Westwood ............... 549/359 |
| 2002/0124613 A1 | | 9/2002 | Sower |
| 2002/0174697 A1 | * | 11/2002 | Reid et al. .............. 71/23 |
| 2004/0065127 A1 | | 4/2004 | Connell |

FOREIGN PATENT DOCUMENTS

| | | | |
|---|---|---|---|
| EP | 000117223 A1 | | 8/1984 |
| KR | 2002-0042013 | * | 6/2002 |

* cited by examiner

*Primary Examiner*—Wayne Langel
(74) *Attorney, Agent, or Firm*—Jeffrey D. Myers; Samantha A. Updegraff; Peacock Myers, P.C.

(57) ABSTRACT

The present invention provides a method for extracting fulvic acid from complexes of humic substances. The fulvic acid extract is safe for human and animal consumption and for application to plant foliage. As a result of the extraction method, the fulvic acid extract further comprises calcium and may comprise magnesium.

8 Claims, No Drawings

EXTRACTION OF FULVIC MINERALS FROM HUMIC SUBSTANCES

CROSS-REFERENCE TO RELATED APPLICATION

This application claims the benefit of the filing of U.S. Provisional Application No. 60/580,070 entitled "Extraction of Fulvic Acid from Humic Substances", filed Jun. 15, 2004, and the specification of that application is incorporated herein by reference.

BACKGROUND OF THE INVENTION

1. Field of the Invention (Technical Field)

The present invention relates to a method for extracting fulvic acid from complexes of humic substances.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Humic substances, hereinafter also referred to collectively as humic substances material(s), are characterized as high molecular weight heterogeneous organic substances that are the components of soils and sediments. Specifically, they are the compounds of which humus is comprised. They are widespread and generally found in areas where there has been dense prehistoric plant growth. They are understood to play an important role in many geo-chemical reactions and processes including the transport of metal ions, contribution to the cation and anion exchange capacity of peat, soil, and water, the water holding capacity of soil, and the binding of various organic molecules.

Because they play a vital role in soil ecosystems, humic substances are considered to be necessary constituents of soil, both for healthy plant growth and for the nutrition of livestock. The practice of agriculture, however, depletes soils of nutrients. It is generally believed that there is widespread mineral nutrient depletion in farm and range soils. Consequently, humic substances are introduced to agricultural soils as fertilizer.

In recognition that humic substances are superior fertilizers, there is an interest in the direct application of some of these substances to plants, and of feeding these to animals. Also, the vitamin and mineral supplement industry is utilizing these substances to supplement human diets that are believed to be deficient in these substances because of their increasingly diminishing concentrations in produce.

Several components of humic substances are believed to be especially beneficial, humic acid and fulvic acid. These are operationally defined in terms of their solubility. Humic acid is the fraction of humic substances that is not soluble in water under acidic conditions but is soluble in water under alkaline conditions. Fulvic acid comprises the fraction of humic substances that is soluble under all pH conditions.

It is believed that because fulvic acid molecules are of a relatively small size, they are more readily absorbed by plants and can carry trace minerals from plant surfaces into plant tissues. Therefore, fulvic acids may be sprayed onto plants to maximize the productive capacity of plants. Fulvic acid is also believed to be of benefit to humans and may be taken orally in liquid form.

However, the methods currently employed for extracting fulvic acid from the other humic substances result in liquids with high pH containing such compounds as phosphoric acid or sulfuric acid. One method, for example, comprises the addition of phosphoric acid or sulfuric acid to a humic substances material in water. A method is needed to extract fulvic acid in a solution that can be safely consumed by humans and animals and/or sprayed on foliage.

BRIEF SUMMARY OF THE INVENTION

One of the embodiments of the present invention provides a method for extracting fulvic acid. The method includes putting humic substances in an aqueous solution, adding to the solution a basic compound that is safe to humans and animals thereby increasing the pH of the solution, allowing the pH to drop over time, and removing the supernatant.

According to another embodiment of the present invention, increasing the pH of the solution comprises raising the pH to between approximately 8.0 and 11, more preferably to a pH of between approximately 8.5 and 10.5, still more preferably to a pH of between approximately 9.0 and 10.0, and most preferably to a pH of approximately 10.0.

Yet another embodiment of the present invention provides for preferably raising the pH of the solution by adding calcium hydroxide. The pH may be increased by adding lime. The pH may be increased by adding calcium hydroxide with magnesium hydroxide.

Preferably, allowing the pH to drop comprises allowing the pH to drop to between approximately 5.5 and 8.0. More preferably, the pH is allowed to drop to between approximately 6.5 and 7.0.

Another embodiment of the present invention provides for a composition comprising fulvic acid extracted from humic substances and calcium. The composition preferably further comprises magnesium. The composition is safe for human and animal consumption and is applicable to plant foliage.

Another embodiment of the present invention provides for a composition consisting essentially of fulvic acid extracted from humic substances and calcium, wherein the composition is safe for human and animal consumption and is applicable onto plant foliage. The composition preferably further consists essentially of magnesium.

It is an object of the invention to provide a fulvic acid extract that is safe for human and animal consumption and for application onto foliage.

It is another object of the invention to provide a fulvic acid extract that comprises certain nutrients such as calcium and magnesium Other objects, advantages and novel features, and further scope of applicability of the present invention are set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

One embodiment of the present invention provides a method for extracting fulvic acid from complexes of humic substances. In the preferred embodiment of the invention, a complex of humic substances, or humic substances material, is placed in solution utilizing water. The pH of the solution is increased.

In another embodiment of the present invention, the pH is increased to between approximately 8.0 and 11.0, more preferably from between approximately 8.5 and 10.5, still more preferably from between approximately 9.0 and 10.0, and most preferably approximately 10. Preferably, this is accomplished by the addition of calcium hydroxide. In another embodiment, lime may be utilized. In still another embodiment, magnesium hydroxide may be introduced together with the calcium hydroxide.

When the desired pH is reached, the solution is allowed to sit. The pH is allowed to drop naturally over time. When the pH drops, the supernatant is removed. Preferably, the supernatant is removed when a pH of between approximately 5.5 and 8.0 is reached, more preferably when a pH of between approximately 6.5 and 7.0 is reached. The supernatant contains the fulvic acid fraction in solution with calcium hydroxide. The solution may be safely consumed or applied to foliage.

The present invention not only provides for the separation of fulvic acid from the other humic substances material compounds, but also provides for the presence of the essential nutrients, calcium and magnesium (if magnesium hydroxide is utilized), in the resulting product.

EXAMPLE

An extract of fulvic acid was obtained using the methods of the present invention. The extract proved safe for animal and human consumption and contained calcium and magnesium as a consequence of the methods of extraction.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A method for extracting fulvic minerals comprising:
   putting humic substances in an aqueous solution;
   adding to the aqueous solution a basic compound to increase the pH of the aqueous solution, wherein the basic compound is safe to humans and animals and comprises a compound selected from the group consisting of calcium hydroxide, magnesium hydroxide, and combinations thereof;
   dropping the pH naturally over time by allowing the solution to sit;
   removing a supernatant comprising a fulvic mineral fraction in a basic solution; and
   providing the fulvic mineral fraction in the basic solution for safe consumption and/or application to foliage.

2. The method of claim 1 wherein the step of increasing the pH of the solution comprises raising the pH to between approximately 8.0 and 11.

3. The method of claim 1 wherein the step of increasing the pH of the solution comprises raising the pH to between approximately 8.5 and 10.5.

4. The method of claim 1 wherein the step of increasing the pH of the solution comprises raising the pH to between approximately 9.0 and 10.0.

5. The method of claim 1 wherein the step of increasing the pH of the solution comprises raising the pH to approximately 10.0.

6. The method of claim 1 wherein the pH of the solution is increased by adding calcium hydroxide.

7. The method of claim 1 wherein the step of dropping the pH comprises dropping the pH naturally to between approximately 5.5 and 8.0.

8. The method of claim 1 wherein the step of dropping the pH naturally comprises dropping the pH naturally to between approximately 6.5 and 7.0.

* * * * *